US008415135B2

(12) United States Patent
Lin

(10) Patent No.: US 8,415,135 B2
(45) Date of Patent: Apr. 9, 2013

(54) LACTOBACILLUS PLANTARUM AND USES THEREOF

(75) Inventor: Wen-Hsin Lin, Taichung (TW)

(73) Assignee: China Medical University, Taichung (TW)

( * ) Notice: Subject to any disclaimer, the term of this patent is extended or adjusted under 35 U.S.C. 154(b) by 98 days.

(21) Appl. No.: 12/868,136

(22) Filed: Aug. 25, 2010

(65) Prior Publication Data

US 2012/0020943 A1 Jan. 26, 2012

(30) Foreign Application Priority Data

Jul. 20, 2010 (TW) .............................. 99123851 A

(51) Int. Cl.
*A61K 38/54* (2006.01)
*C12N 1/20* (2006.01)

(52) U.S. Cl. .................................. 435/252.9; 424/93.45

(58) Field of Classification Search ........................ None
See application file for complete search history.

(56) References Cited

U.S. PATENT DOCUMENTS

| 3,953,609 A | 4/1976 | Farr |
| 5,603,930 A | 2/1997 | Brassart et al. |
| 6,491,956 B2 | 12/2002 | Heo et al. |
| 2005/0271643 A1* | 12/2005 | Sorokulova et al. ..... 424/93.462 |
| 2008/0268006 A1* | 10/2008 | Molin et al. .................. 424/402 |

FOREIGN PATENT DOCUMENTS

KR 2003-0077895 10/2003

OTHER PUBLICATIONS

English language translation of abstract of TW 200611973 (p. 3 of publication).
English language translation of abstract of TW 200708622 (p. 3 of publication).
Comparison of KR 2003-0077895 with U.S. Appl. No. 12/868,136 and related attachments.
Korea Office Action issued Mar. 16, 2012.

* cited by examiner

*Primary Examiner* — Blaine Lankford
*Assistant Examiner* — Lauren K Van Buren
(74) *Attorney, Agent, or Firm* — McClure, Qualey & Rodack, LLP

(57) ABSTRACT

Provided is an isolated *Lactobacillus plantarum* CMU995, which was deposited at the Food Industry Research and Development Institute in Taiwan with the accession number BCRC 910472 and in the German Collection of Microorganisms and Cell Cultures (DSMZ) under accession number DSM 23780. Also provided are a composition comprising *Lactobacillus plantarum* CMU995 and a method for inhibiting pathogens, protecting the gastrointestinal tract, and/or protecting the urinary tract in a mammal comprising administrating an effective amount of *Lactobacillus plantarum* CMU995 to the mammal.

16 Claims, 1 Drawing Sheet

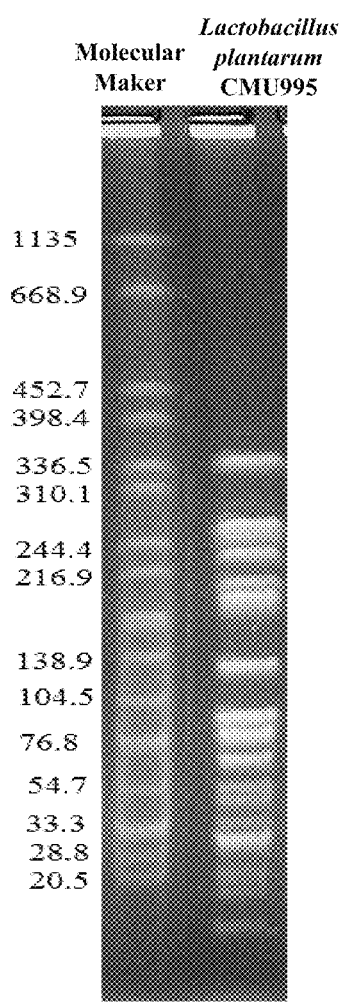

LACTOBACILLUS PLANTARUM AND USES THEREOF

This application claims priority to Taiwan Patent Application No. 099123851 filed on Jul. 20, 2010.

CROSS-REFERENCES TO RELATED APPLICATIONS

Not applicable.

BACKGROUND OF THE INVENTION

1. Field of the Invention

The present invention relates to a *Lactobacillus plantarum* strain and uses thereof, especially to an isolated *Lactobacillus plantarum* CMU995 and uses thereof.

2. Descriptions of the Related Art

*Lactobacillus* is one of the main bacteria existed in the intestinal tract of a human being or an animal. Due to the beneficial effects on the physiological activity of a human or an animal body, *Lactobacillus* is often added into various probiotic products. For example, *Lactobacillus* can inhibit the growth of enteric pathogens (such as *Salmonella* or *Escherichia*) or resist pathogen invasion, for instance, preventing an invasion of *Salmonella typhimurium* to the gastrointestinal epithelial cells.

Currently, there are many patents relating to the applications of *Lactobacillus* for inhibiting pathogens. For example, U.S. Pat. No. 5,603,930 discloses a *Lactobacillus johnsonii* that can inhibit enterotoxin and intestinal invasive pathogens; U.S. Pat. No. 3,953,609 discloses a *Lactobacillus* lactis that can inhibit the growth of *Escherichia* in the digestive system; and U.S. Pat. No. 6,491,956 discloses a *Lactobacillus acidophilus* that can prevent and treat gastritis, duodenal ulcer, and gastric ulcer caused by *Helicobacter pylori* infection.

Apart from basic physiological/pharmacological activity, *Lactobacillus* must have two important characteristics to function effectively within the animal body. Firstly, the *Lactobacillus* must have strong tolerance to the gastric acid and choline secreted by the animal gastrointestinal tract in order to survive in the digestive system and reach to the intestinal tract to serve its function. Then, the *Lactobacillus* must be able to strongly adhere to the intestinal epithelial cells of an animal host to compete with other pathogens in the gastrointestinal tract and avoid being expelled by the pathogens. In addition, because pathogens also infect the animal body by adhering onto the intestinal epithelial cells, if the *Lactobacillus* has a relatively strong adhesion ability to the intestinal epithelial cells, then it can expel the pathogens to protect the gastrointestinal tract from being infected.

The inventor of the present invention screened a novel strain of *Lactobacillus plantarum* from the excretion of newborn babies, and through relative in vivo and in vitro experiments, found that apart from inhibiting pathogens, the *Lactobacillus plantarum* has excellent adhesion ability to the cells of the gastrointestinal tract and the urinary tract, and therefore can effectively and durably protect the gastrointestinal tract and the urinary tract from pathogenic infections. The inventor also found that this strain can directly inhibit the growth of pathogens to prevent and treat diseases caused by the pathogens.

SUMMARY OF THE INVENTION

The primary objective of the present invention is to provide an isolated *Lactobacillus plantarum* CMU995, deposited in the Food Industry Research and Development Institute (FIRDI) at 331 Shih-Pin Road, Hsinchu, Taiwan on Apr. 30, 2010 under the accession number BCRC 910472, and in the German Collection of Microorganisms and Cell Cultures (DSMZ) at Inhoffenstr. 7B, D-38124 Braunschweig (Germany) on Jul. 15, 2010 under accession number DSM 23780. The deposit at the DSMZ was made under the provisions of the Budapest Treaty on the International Recognition of the Deposit of Microorganisms for the Purposes of Patent Procedure.

Another objective of the present invention is to provide a composition comprising the *Lactobacillus plantarum* CMU995.

Yet a further objective of the present invention is to provide a method for inhibiting pathogens, protecting the gastrointestinal tract, and/or protecting the urinary tract in a mammal, comprising administrating an effective amount of *Lactobacillus plantarum* CMU995 to the mammal.

The detailed technology and preferred embodiments implemented for the present invention are described in the following paragraphs accompanying the appended drawings for people skilled in this field to well appreciate the features of the claimed invention.

BRIEF DESCRIPTION OF THE DRAWINGS

FIG. 1 shows a gene fingerprinting map of *Lactobacillus plantarum* CMU995.

DESCRIPTION OF THE PREFERRED EMBODIMENT

The inventor of the present invention screened and isolated a novel *Lactobacillus* strain from the excretion of healthy newborn babies, and the strain was identified as *Lactobacillus plantarum* and named as *Lactobacillus plantarum* CMU995.

As described above, *Lactobacillus* must be able to strongly adhere to the intestinal epithelial cells of animal hosts to compete with pathogens for adhesion to the gastrointestinal tract, and further expel the pathogens to achieve desired physiological effects. It was discovered that *Lactobacillus plantarum* CMU995 can attach onto the gastrointestinal epithelial cells, with an even stronger adhesion ability to the gastrointestinal epithelial cells than that of *Lactobacillus rhamnosus* GG (LGG) which is commonly seen in the market.

Apart from adhering onto the gastrointestinal epithelial cells, *Lactobacillus plantarum* CMU995 can also adhere firmly onto the urinary epithelial cells, and therefore can compete with pathogens for adhesion to the urinary tract, and further eliminate the pathogens to protect the urinary tract.

Because *Lactobacillus plantarum* CMU995 has good adhesion to the gastrointestinal tract and the urinary tract, it can be used to prevent or treat pathogen infections. For prevention, *Lactobacillus plantarum* CMU995 can be added to feeds, drinks, nutritional supplements, or health foods, so that the strain can adhere onto the gastrointestinal tract or the urinary tract to protect people who consume these products. When pathogens invade the gastrointestinal tract or the urinary tract, they cannot compete with *Lactobacillus plantarum* CMU995 for adhesion, and therefore cannot initiate the infection mechanism, and are further expelled out of the body. For treatment, when the gastrointestinal tract or the urinary tract of the human body or the animal body is infected by pathogens, for example, a medicament comprising *Lactobacillus plantarum* CMU995 can be taken, wherein the pathogens that are adhered on the gastrointestinal tract or the urinary tract will be eliminated by the adsorption characteristic of *Lactobacillus plantarum* CMU995 to the gastrointestinal tract and the urinary tract to achieve treatment effects. Therefore, *Lactobacillus plantarum* CMU995 can inhibit pathogens from adhering onto cells of the gastrointestinal tract or the urinary tract through the strong adsorption ability thereof to prevent or treat the infection of pathogens.

Apart from inhibiting the adhesion of pathogens onto the gastrointestinal tract or the urinary tract to indirectly inhibit the infection, *Lactobacillus plantarum* CMU995 can directly inhibit the growth of pathogens, and thus it can protect the gastrointestinal tract and/or the urinary tract by the synergism of these two inhibition mechanisms. Therefore, the phrase "inhibiting pathogens" in this text comprises the inhibition of the adhesion of pathogens onto the gastrointestinal tract, the inhibition of the adhesion of pathogens onto the urinary tract, and the inhibition of the growth of pathogens.

*Lactobacillus plantarum* CMU995 can be used to inhibit the variety of pathogens in the gastrointestinal tract and/or the urinary tract. For example, it can inhibit pathogens selected from a group consisting of *Helicobacter pylori, Campylobacter jejuni, Salmonella* spp., *Escherichia* spp., *Staphylococcus* spp., *Shigella flexneri, Clostridium perfringens, Candida albicans*, and combinations thereof. Particularly, it can be used to inhibit *Helicobacter pylori*.

*Helicobacter pylori* are Gram-negative, microaerophilic pathogens and can survive in various regions of the stomach and the duodenum. The transmission pathway of *Helicobacter pylori* is still unclear up-to-date, but it can lead to gastric mucosal chronic inflammation, resulting in gastric ulcer and duodenal ulcer or even gastric cancer. Therefore, the world health organization (WHO) announced that *Helicobacter pylori* is a type of carcinogenic microorganism, and is also the first prokaryote that was found to be carcinogenic. More than half of the world population are *Helicobacter pylori* carriers, and most are living in developing countries. Currently, the main approach for treating diseases induced by *Helicobacter pylori* is by using antibiotics. However, because of the drug resistance of *Helicobacter pylori*, many antibiotics no longer achieve satisfactory treatment results. Because *Lactobacillus plantarum* CMU995 can remarkably inhibit the growth of *Helicobacter pylori* and its adhesion to the intestinal epithelial cells, it can be used to combine or even replace the traditional usage of antibiotics to effectively prevent or treat a variety of diseases caused by *Helicobacter pylori*.

In addition, because *Lactobacillus plantarum* CMU995 can directly inhibit the growth of pathogens, it can be used to prevent and treat diseases caused by the pathogens, and the diseases are not just limited to gastrointestinal diseases. For example, it is known that *Staphylococcus* spp. may infect the gastrointestinal tract as well as other areas such as the respiratory tract, urinary tract, vein, wound, etc., and thus, the inhibition of the growth of *Staphylococcus* spp. by *Lactobacillus plantarum* CMU995 can be applied to treat and prevent infections of the aforesaid areas. In another aspect, *Candida albicans* may infect the gastrointestinal tract as well as mucosal tissues of the oral cavity, urinary tract, etc., and thus the inhibition of the growth of *Candida albicans* by *Lactobacillus plantarum* CMU995 can be applied to the treatment or prevention of the infections of the oral cavity or urinary tract.

Due to the adsorption characteristic and ability to inhibit the pathogen growth of *Lactobacillus plantarum* CMU995, it can be widely applied in various medical and health products. Therefore, the present invention also provides a composition comprising *Lactobacillus plantarum* CMU995. Based on the aforesaid special character of *Lactobacillus plantarum* CMU995, the composition of the present invention can be used to inhibit pathogens, protect the gastrointestinal tract, protect the urinary tract, or combinations thereof.

The composition of the present invention can be prepared in any form. For example, it can be prepared in a form selected from a group consisting of pharmaceutical compositions, feeds, drinks, nutrition supplements, diary products, foods, health foods, sprays, and suppositories. In an embodiment of the present invention, *Lactobacillus plantarum* CMU995 can be added into food products, for instance, diary products. The applications of *Lactobacillus* in pharmaceutical compositions and food products can be seen in Taiwan Laid-Open Patent No. 200708622 and Taiwan Laid-Open Patent No. 200611973, which are entirely incorporated hereinto as reference.

The composition of the present invention can be optionally added with any suitable additives to further enhance the effects of adhesion and inhibition of pathogen growth. Alternatively, other nutrients or pharmaceutical components can be added into the composition to increase the flexibility of the applications. For example, the composition of the present invention may contain one or more active ingredients such as antacids, other probiotics, etc., as long as these active ingredients have no adverse effects towards the efficacy of *Lactobacillus plantarum* CMU995.

The present invention also provides a method for inhibiting pathogens, protecting the gastrointestinal tract, and/or protecting the urinary tract in a mammal, comprising administrating an effective amount of the *Lactobacillus plantarum* CMU995 to the mammal.

Hereinafter, the present invention will be further illustrated with reference to the following examples. However, these examples are only provided for illustrate purpose, but not to limit the scope of the present invention.

EXAMPLE 1

Adhesion Analysis

Experiment A

Preparation of *Lactobacillus* Strains

*Lactobacillus* strains used to conduct the adhesion analysis of the gastrointestinal cells include: *Lactobacillus plantarum* CMU995, *Lactobacillus rhamnosus* GG (LGG), and *Lactobacillus* strains B7P3, A7G1, B1T4, IA5, and HT5 isolated from the laboratory. All the *Lactobacillus* strains were activated with an MRS culture solution (Difco, Detroit, Mich., USA) twice, and they were transferred and cultured in an MRS culture solution (5 mL). After 24 hours, 1 mL of the broth was taken and centrifuged (6000 rpm) for 10 minutes and rinsed twice with a phosphate buffer solution (PBS, pH 7.2) to proceed the following adhesion experiment. *Lactobacillus rhamnosus* GG was used as the control group.

Experiment B

Cell Culture of the Gastrointestinal Tract and the Urinary Tract Cell Lines

The gastrointestinal tract cell lines that were used in this experiment were Caco-2 human colon adenocarcinoma (Accession Number: ATCC CRL 2102) and AGS gastric adenocarcinoma (Accession Number: ATCC CRL1739). The urinary tract cell lines that were used were Hela human cervical epithelial cells (Accession Number: ATCC CCL-2), which were all purchased from the Bioresource Collection and Research Center (BCRC), Taiwan, and had already passed the contamination test of bacteria, mycete, and mycoplasma. After the cell lines were obtained, they were immediately transferred into a water bath at 37° C. under constant temperature and thawed, and cultured in a 25 cm² petri dish, and then placed and cultured in a cell incubator containing 5 vol % carbon dioxide at 37° C. The cells were activated and subcultured several times, and further experiments were carried out after the cell lines were stable. The culture medium of Caco-2 cells was Dulbecco's Modified Eagle Medium (DMEM, purchased from Gibco Corp); the culture medium of AGS cells was F-12 medium (purchased from Gibco Corp); and the culture medium of Hela cells was Minimum Essential Medium (MEM, purchased from Gibco Corp). All the above culture mediums had added 10 vol % fetal bovine serum (FBS).

Experiment C

Adhesion Analysis of *Lactobacillus*

The cell lines prepared from Experiment B were treated with 0.05 vol % trypsin (1 mL) for 5 minutes, and were transferred to a 96-well plate wherein 1×10⁴ cells were added into each well, and the medium was replaced by a fresh medium (200 mL) each day. Then, the *Lactobacillus* broth prepared in Experiment A (20 μL) was added into the cells and cultured for 1 hour to allow *Lactobacillus* to adhere onto the cells. After an hour of adhesion, the medium was removed, and the cells were rinsed with a phosphate buffer solution (PBS) five times to remove *Lactobacillus* that did not adhere on the cells, and 10 vol % formalin (100mL) was added to stabilize the cells and *Lactobacillus*. After 30 minutes, the cells were rinsed with PBS three times, and finally stained with crystal violet (100 μL) for 5 minutes, and immediately washed with a minimum amount of 75 vol % alcohol to remove the stain on the cells.

A phase contrast microscopy was used to observe the adhesion ability of various *Lactobacillus* onto the epithelial cells of the gastrointestinal tract or the urinary tract, and under randomized microscopic areas, the adhesion of *Lactobacillus* onto fifty cells was observed and calculated, and the average amount of *Lactobacillus* adhering to each cell was calculated. The results are shown in Table 1.

TABLE 1

| | The number of adhered *Lactobacillus* (CFU/cell) | | |
|---|---|---|---|
| Strains | Caco-2 | AGS | Hela |
| CMU995 | >30 | >30 | 27 ± 2.3 |
| LGG | 7.5 ± 1.5 | 4.4 ± 0.8 | 5.1 ± 1.2 |
| B7P3 | >30 | 25.8 ± 2.4 | 26 ± 3.1 |
| A7G1 | >30 | >30 | 22.5 ± 2.4 |
| B1T4 | 18.4 ± 3.9 | 15.2 ± 2.3 | 16.7 ± 3.1 |
| IA5 | 16.7 ± 2.6 | 18.9 ± 2.8 | 18.4 ± 4.0 |
| HT5 | 17.4 ± 1.2 | 19.0 ± 0.8 | 15.4 ± 2.3 |
| Other strains (around 3000 strains) | <10 | <10 | <10 |

As can be seen from Table 1, compared to other known *Lactobacillus* (including *Lactobacillus rhamnosus* GG which is internationally well-known and commonly seen in the market), *Lactobacillus plantarum* CMU995 has even better adhesion ability to the cells of the gastrointestinal tract and the urinary tract, and thus can provide even more long-lasting protection to the gastrointestinal tract and the urinary tract.

EXAMPLE 2

Inhibition Test of the Growth of Pathogens

Experiment D

Petri Dish Test

The well-diffusion method was used to evaluate the inhibition ability of *Lactobacillus* to the pathogen growth. A sterile *Brucella* agar medium (Difco, Detroit, Mich., USA) was poured into a bacteria petri dish and solidified. Then, overnight-cultured, indicative pathogens of the gastrointestinal tract, *Helicobacter pylori* (Accession Number: BCRC 17021) and clinically isolated *Helicobacter pylori* CMU83, were smeared evenly on the agar medium. After the broth was slightly dried, a hole with diameter of 7 mm was made on the petri dish, and the broth (70 μL) of *Lactobacillus plantarum* CMU 995 cultured for 24 hours in the MRS medium in Experiment A was added into the hole. Furthermore, the above method was also used to analyze other gastrointestinal pathogens, comprising *Campylobacter jejuni* CMU20, *Escherichia* spp., *Staphylococcus aureus*, *Salmonella* spp., *Shigella flexneri*, *Clostridium perfringens*, and *Candida albicans*. Each sample was analyzed repetitively three times, and the culture medium was placed into a bacteria incubator, and after 16 to 18 hours, the diameter of the bacteria inhibition zone (circle) was measured. Herein, a fermented solution of *Lactobacillus rhamnosus* GG was used as the positive control, and a MRS medium with pH 6.3 was used as the negative control. The results are shown in Table 2.

TABLE 2

| | Diameter of Bacteria Inhibition Zone/Circle (mm) | | |
|---|---|---|---|
| Pathogens | CMU995 | LGG | MRS medium |
| *Helicobacter pylori* BCRC 17021 | 10.7 ± 0.5 | 10.3 ± 0.5 | — |
| *Helicobacter pylori* CMU83 | 9.0 ± 0.0 | 9.0 ± 0.5 | — |
| *Campylobacter jejuni* CMU20 | 9.7 ± 0.5 | 9.0 ± 0.0 | — |
| Enterotoxigeic *E. coli* (ETEC) | 11.7 ± 0.5 | 11.3 ± 0.5 | — |
| Enteroinvasive *E. coli* (EIEC) | 13.0 ± 0.0 | 12.3 ± 0.5 | — |
| Enteropathogenic *E. coli* (EPEC) | 12.3 ± 0.5 | 12.3 ± 0.5 | — |
| Enteroadherent aggregative *E. coli* (EAggEC) | 12.0 ± 0.8 | 11.7 ± 0.5 | — |
| *Staphylococcus aureus* | 11.3 ± 0.5 | 11.0 ± 0.0 | — |
| *Salmonella enteritidis* | 13.0 ± 0.0 | 12.7 ± 0.5 | — |
| *Salmonella typhimurium* | 13.0 ± 0.8 | 12.3 ± 0.5 | — |
| *Shigella flexneri* | 11.3 ± 0.5 | 10.7 ± 0.5 | — |
| *Clostridium perfringens* | 11.7 ± 0.5 | 11.3 ± 0.5 | — |
| *Candida albicans* | 8.3 ± 0.5 | 8.3 ± 0.5 | — |

"—"represents no inhibition effect.

The results in Table 2 illustrate that, compared to *Lactobacillus rhamnosus* GG, the *Lactobacillus plantarum* CMU995 of the present invention has even better efficacy to inhibit pathogen growth, and thus it can be used to prevent and treat diseases caused by the pathogens. For example, it can be used to protect the gastrointestinal tract from pathogen infections.

EXAMPLE 3

Inhibition Test of Pathogen Infection and Adhesion Test

Caco-2 cells, AGS cells, and Hela cells (each with 1 mL; density: $5\times10^4$ cell/mL) were cultured in a 24-well cell culture plate respectively, and placed in the cell incubator comprising 5 vol % carbon dioxide/95 vol % air at 37° C., and cultured for 2 days, and the following two kinds of tests were conducted.

Experiment E

Prevention and Protection Mode

A fermentation solution (100 µL) of *Lactobacillus plantarum* CMU995 cultured for 24 hours in Experiment A was added to Caco-2 cells, AGS cells, or Hela cells cultured for 2 days and mixed evenly, and the cells were placed into a cell incubator to incubate for 0.5 hour. Then, the cells were rinsed with a sterile saline solution to remove *Lactobacillus* that did not adhere to the cells. *Helicobacter pylori* CMU83, enteroadherent aggregative *E. coli* (EAggEC), or *Salmonella enteritidis* (each with 1 mL, $1\times10^7$ cfu/mL) was added to the cells and mixed evenly, and the cells were placed and cultured in the cell incubator for 1 hour, allowing the pathogens to infect the cells. Then, the medium was removed, and the cells were rinsed with a sterile saline solution to remove the pathogens that did not infect the cells, and 0.1 vol % Triton-X-100 (1 mL) (Sigma, Louis, Mo., USA) was further added to lyse the cells to release the infecting pathogens. Finally, the solution containing the lysed cells was collected and placed in a PBS solution (9 mL). After the solution was appropriately diluted, the pour plate method was used to calculate the number of the bacteria. Herein, an experiment in which the cells were not added with the *Lactobacillus* served as the control group, and the calculation result was applied to the following formula to calculate the infection inhibition rate of *Lactobacillus plantarum* CMU995. The results are shown in Table 3.

Infection Inhibition Rate=(Number of pathogens in the control group−Number of pathogens in the group with addition of *Lactobacillus*)/Number of pathogens in the control group×100%

Experiment F

Treatment and Elimination Mode

Caco-2 cells, AGS cells, or Hela cells were cultured for two days, respectively, and *Helicobacter pylori* CMU83, enteroadherent aggregative *E. coli* (EAggEC), or *Salmonella enteritidis* (each with 1 mL, $1\times10^7$ cfu/mL) was added to the cells, and the cells were cultured for 0.5 hours to allow the pathogens to infect the cells. Then, the cells were rinsed with a sterile saline solution to remove the pathogens that did not invade the cells. A fermented solution (100 µL) of *Lactobacillus plantarum* CMU995 cultured for 24 hours in Experiment A was added to the cells, and the cells were cultured for 1 hour to allow *Lactobacillus plantarum* CMU995 to expel the pathogens. Finally, the cells were rinsed with a sterile saline solution to remove the *Lactobacillus* that did not adhere to the cells and the expelled pathogens. 0.1 vol % Triton-X-100 (1 mL) was added to lyse the cells to release the infecting pathogens. After the solution containing the lysed cells was collected and appropriately diluted, the number of bacteria was calculated by the pour plate method. Herein, an experiment in which the cells were not added with the *Lactobacillus* served as the control group, and the calculation result was applied to the above formula to calculate the infection inhibition rate of *Lactobacillus plantarum* CMU995. The results are shown in Table 4.

TABLE 3

Infection inhibition rate (%) - Prevention and protection mode

| | Caco-2 | AGS | Hela |
|---|---|---|---|
| *Helicobacter pylori* CMU83 | 21.74 | 20.53 | ND |
| EAggEC | 86.35 | ND | 87.50 |
| *Salmonella enteritidis* | 85.10 | ND | 78.24 |

"ND" represents that the cell test was not conducted.

TABLE 4

Infection inhibition rate (%) - Treatment and elimination mode

| | Caco-2 | AGS | Hela |
|---|---|---|---|
| *Helicobacter pylori* CMU83 | 32.02 | 30.80 | ND |
| EAggEC | 99.21 | ND | 96.61 |
| *Salmonella enteritidis* | 99.05 | ND | 98.87 |

"ND" represents that the cell test was not conducted.

As can be seen from Tables 3 and 4, *Lactobacillus plantarum* CMU995 has excellent efficacy in inhibiting pathogen infections. In particular, the results in the treatment and elimination mode clearly showed that *Lactobacillus plantarum* CMU995 can effectively reduce the adhesion of the pathogens to the cells of the gastrointestinal tract and the urinary tract, and further expel the pathogens out of the cells to achieve the effect of inhibiting the infection. Furthermore, *Lactobacillus plantarum* CMU995 also has an excellent inhibition effect towards *E. coli* or *Salmonella* spp.

EXAMPLE 4

Animal Test

Experiment G

Experimental Animal Grouping 6-week old male C57BL/6 mice (purchased from Lasco, Inc., Taiwan) were used in this experiment. The weight of the mice ranged from 20 to 26 g and the mice were bred in an independent IVC mice breeding system where the temperature was sustained at 22° C. with regularly 12-hour light and dark. The mice were fed with sterilized feed and reverse osmosis water and fed freely. Before initiating the experiment, these mice were fed for two weeks to let the mice adjust to the environment. The mice were randomly classified into 4 groups with 8 mice in a group. Before being infected by *Helicobacter pylori*, the mice in each group were orally fed with a 200 µL of different concentrations of freshly prepared *Lactobacillus plantarum* CMU995 broth at a particular time for 7 days continuously and fed once daily. The condition of the experiment of each group is listed below:

Group A: Physiological Saline Solution/Negative Control Group

The mice were fed by a sterile filtrated physiological saline solution.

Group B: $1\times10^{10}$ Colony Forming Unit (cfu)/mL of *Lactobacillus plantarum* CMU995 Group

*Lactobacillus plantarum* CMU995 was cultured with a MRS culture solution for 24 hours, and the broth was collected and centrifuged and then re-dissolved with a physiological saline solution. The bacteria concentration was adjusted to $1\times10^{10}$ cfu/mL, and then the bacteria were fed to the mice.

Group C: $1\times10^{9}$ cfu/mL of *Lactobacillus plantarum* CMU995 Group

*Lactobacillus plantarum* CMU995 was cultured with a MRS culture solution for 24 hours, and the broth was collected and centrifuged and then re-dissolved with a physiological saline solution. The bacteria concentration was adjusted to $1\times10^{9}$ cfu/mL, and the bacteria were then fed to the mice.

Group D: $1\times10^{8}$ cfu/mL of *Lactobacillus plantarum* CMU995 Group

*Lactobacillus plantarum* CMU995 was cultured with a MRS culture solution for 24 hours, and the broth was collected and centrifuged and then re-dissolved with a physiological saline solution. The bacteria concentration was adjusted to $1\times10^{8}$ cfu/mL, and the bacteria were then fed to the mice.

Experiment H

*Helicobacter pylori* Infection Test

After the mice were fed with a *Lactobacillus plantarum* CMU995 broth for 7 days, on the next day, the mice were orally fed with a broth containing $2\times10^{7}$ colony forming unit (cfu) of *Helicobacter pylori* CMU83. The mice were fed continuously for 3 days to trigger infection, and on the next day, the mice were fasted for 1 day. Then, the mice were sacrificed with carbon dioxide, with their cervix and vertebra separated. The stomachs and the duodenum sections (approximately 0.5 g) of the mice were taken and placed into an eppendorf tube containing 9.5 mL of a sterile PBS solution, and were agitated with a homogenizer for 3 minutes. The solution (1 mL) containing the fragmented tissues was taken and then diluted by 10-fold continuously with a sterile PBS solution. The diluted solutions (100 μL) with different dilution fold were taken, and were respectively spread onto a *Brucella* agar medium by the Spread-plate method, and 2.5 vol % fetal bovine serum and the Selective Supplements SR147E (Oxoid, Hampshire, England) for screening *Helicobacter pylori* were added to the medium. This medium was tested and confirmed to be able to screen *Helicobacter pylori* CMU83 used in the present experiment. The medium was placed under a microaerobic condition for 48 hours at 37° C. to incubate the bacteria, and the colony forming unit (cfu) of the bacteria was calculated. The statistical analysis of each experiment was repeated 3 times, and the experiment results were analyzed by SPSS 10.0 software. First, one way ANOVA (analysis of variance) was used to test the significant difference between each group, and the standard was $p<0.05$. The results are shown in Table 5.

TABLE 5

| | Group | | | |
|---|---|---|---|---|
| | A Physiological saline solution | B $1\times10^{10}$ cfu/mL | C $1\times10^{9}$ cfu/mL | D $1\times10^{8}$ cfu/mL |
| Average number of infecting bacteria (Log cfu/tissue) | 3.71 ± 0.79 | 1.91 ± 0.90* | 2.65 ± 1.29* | 2.91 ± 0.74 |

"*": represents a significant difference ($P<0.05$) in comparison with the physiological saline solution group.

Table 5 shows that after the mice were fed with a concentration of $1\times10^{9}$ cfu/mL or $1\times10^{10}$ cfu/mL of *Lactobacillus plantarum* CMU995, the infection of *Helicobacter pylori* to the gastrointestinal tracts of the mice was remarkably inhibited, and thus *Lactobacillus plantarum* CMU995 can achieve the efficacy to protect the gastrointestinal tract from pathogenic infection.

EXAMPLE 5

Experiment I

Identification of the Strain

[*Lactobacillus* Identification Kit Analysis]

*Lactobacillus plantarum* CMU995 of the present invention was activated and incubated with a MRS culture medium for 16 hours, and an API 50 CHL Identification Kit (Biomerieux, Marcy I'Etoile, Frace) specializing in identification of *Lactobacillus* was used to analyze and confirm the species of the strain.

[Gene Sequencing Analysis]

A specific primer for *Lactobacillus* was used to carry out the polymerase chain reaction (PCR) of 16S-23 S rRNA sections of *Lactobacillus plantarum* CMU995, and the sequence of the resultant product was analyzed. The sequence of the obtained PCR product was analyzed, and part of the sequence is shown in SEQ ID NO: 1.

```
                                              SEQ ID NO: 1
ACATTGCAACAGCGCGTGCCGTATTTTAATTATCGGCTAGCCACAGAGAT

CTATCCGTTAAACAAACAATTTACTGAGAAATACGGGAATAAGTATGGGA

AATATCCCTAGCGAACCCTAAATAATGGCCCCCCTGTCTTGAACAGATAG

ACTGGCCAAACTCCTACGGGAGAAAACGTTGGGAAATTTTGCTCAATGGG

CCCAACCCTGAGGCGCCCCTGCCACATATATGAGGAAAGCCTTCGGGTTA

TAAAATTTTTTTTCAGCGAGGAGTGAAGTGAGGATAAGAACCTTCTACA
```

The primers used in the present analysis were LU-5 and Lac-2. The sequences are shown below:

```
LU-5:    5'-CTAGCGGGTGCGACTTTGTT-3'    SEQ ID NO: 2

Lac-2:   5'-CCTCTTCGCTCGCCGCTACT-3'    SEQ ID NO: 3
```

[Pulsed Field Gel Electrophoresis (PFGE) Analysis]

Pulsed Field Gel Electrophoresis was used to analyze the genomic DNA of *Lactobacillus plantarum* CMU995, and SgsI (Promega Corporation, Madison, USA) was used as the restriction enzyme to obtain a genetic fingerprinting map of Lactobacillus plantarum CMU995, and the result is shown in FIG. 1. The genetic fingerprinting map in FIG. 1 is only provided as a reference for the genetic fingerprinting identification of Lactobacillus plantarum CMU995 but not provided for limiting the gene identification result of the strain.

tion as described without departing from the characteristics thereof. Nevertheless, although such modifications and replacements are not fully disclosed in the above descriptions, they have substantially been covered in the following claims as appended.

SEQUENCE LISTING

```
<160> NUMBER OF SEQ ID NOS: 3

<210> SEQ ID NO 1
<211> LENGTH: 299
<212> TYPE: DNA
<213> ORGANISM: Lactobacillus plantarum

<400> SEQUENCE: 1
acattgcaac agcgcgtgcc gtattttaat tatcggctag ccacagagat ctatccgtta      60
aacaaacaat ttactgagaa atacgggaat aagtatggga aatatcccta gcgaacccta     120
aataatggcc ccoctgtctt gaacagatag actggccaaa ctcctacggg agaaaacgtt    180
gggaaatttt gctcaatggg cccaaccctg aggcgcccct gccacatata tgaggaaagc    240
cttcgggtta taaaattttt tttcagcgag gagtgaagtg aggataagaa ccttctaca    299

<210> SEQ ID NO 2
<211> LENGTH: 20
<212> TYPE: DNA
<213> ORGANISM: Artificial Sequence
<220> FEATURE:
<223> OTHER INFORMATION: chemically synthesized primer sequence

<400> SEQUENCE: 2
ctagcgggtg cgactttgtt                                                 20

<210> SEQ ID NO 3
<211> LENGTH: 20
<212> TYPE: DNA
<213> ORGANISM: Artificial Sequence
<220> FEATURE:
<223> OTHER INFORMATION: chemically synthesized primer sequence

<400> SEQUENCE: 3
cctcttcgct cgccgctact                                                 20
```

According to the result of the API 50 CHL identification kit, it shows that Lactobacillus plantarum CMU995 belongs to Lactobacillius plantarum. The comparative result for the gene sequence of the PCR product further proves that this strain is a novel Lactobacillus plantarum.

Lactobacillus plantarum CMU995 was deposited at the Food Industry Research and Development Institute (FIRDI) in Taiwan under accession number BCRC 910472 and in the German Collection of Microorganisms and Cell Cultures (DSMZ) under accession number DSM 23780.

The above examples revealed that Lactobacillus plantarum CMU995 can inhibit the adhesion of pathogens to the gastrointestinal tract and the urinary tract to protect cells of the gastrointestinal tract and reduce pathogenic infection, and it can also directly inhibit the growth of pathogens, and thus it can protect the gastrointestinal tract and the urinary tract by the synergism effect of these two inhibition mechanisms.

The above disclosure is related to the detailed technical contents and inventive features thereof. People skilled in this field may proceed with a variety of modifications and replacements based on the disclosures and suggestions of the inven-

What is claimed is:

1. An isolated Lactobacillus plantarum CMU995, deposited at the Food Industry Research and Development Institute (FIRDI) in Taiwan under accession number BCRC 910472 and in the German Collection of Microorganisms and Cell Cultures (DSMZ) under accession number DSM 23780.

2. The Lactobacillus plantarum CMU995 as claimed in claim 1, which is able to adhere onto a gastrointestinal tract and/or a urinary tract in a mammal.

3. The Lactobacillus plantarum CMU995 as claimed in claim 2, wherein the mammal is a human being.

4. The Lactobacillus plantarum CMU995 as claimed in claim 1, which is able to inhibit the growth of a pathogen in a mammal.

5. The Lactobacillus plantarum CMU995 as claimed in claim 4, wherein the pathogen is selected from the group consisting of Helicobacter pylori, Campylobacter jejuni, Salmonella spp., Escherichia spp., Staphylococcus spp., Shigella flexneri, Clostridium perfringens, Candida albicans, and combinations thereof.

6. The Lactobacillus plantarum CMU995 as claimed in claim 5, wherein the pathogen is Helicobacter pylori.

7. The *Lactobacillus plantarum* CMU995 as claimed in claim 4, wherein the mammal is a human being.

8. The *Lactobacillus plantarum* CMU995 as claimed in claim 1, which is able to inhibit a pathogen from adhering onto a gastrointestinal tract and/or a urinary tract in a mammal.

9. The *Lactobacillus plantarum* CMU995 as claimed in claim 8, wherein the pathogen is selected from the group consisting of *Helicobacter pylori, Campylobacter jejuni, Salmonella* spp., *Escherichia* spp. *Staphylococcus* spp., *Shigella flexneri, Clostridium perfringens, Candida albicans*, and combinations thereof.

10. The *Lactobacillus plantarum* CMU995 as claimed in claim 9, wherein the pathogen is *Helicobacter pylori*.

11. The *Lactobacillus plantarum* CMU995 as claimed in claim 8, wherein the mammal is a human being.

12. A composition comprising the *Lactobacillus plantarum* CMU 995 as claimed in claim 1.

13. The composition as claimed in claim 12, which is used for inhibiting a pathogen, protecting a gastrointestinal tract, and/or protecting a urinary tract in a mammal.

14. The composition as claimed in claim 13, wherein the pathogen is selected from the group consisting of *Helicobacter pylori, Campylobacter jejuni, Salmonella* spp., *Escherichia* spp., *Staphylococcus* spp., *Shigella flexneri, Clostridium perfringens, Candida albicans*, and combinations thereof.

15. The composition as claimed in claim 13, wherein the pathogen is *Helicobacter pylori*.

16. The composition as claimed in claim 12, wherein the composition is a pharmaceutical composition, a feed, a drink, a nutritional supplement, a diary product, a food, a health food, a spray, or a suppository.

* * * * *